United States Patent [19]
Webb et al.

[11] Patent Number: 5,633,007
[45] Date of Patent: May 27, 1997

[54] SURGICAL DRESSING

[75] Inventors: Julian Webb, Clifton; Christopher I. Reed, Southbank; Mark F. Smith, Huby; David F. Farrar, Fulford; Patrick L. Blott, Hull Road; David Houldridge, Badger Hill; Anna F. MacFarlane, York; Selvarajah Sivshanker, Holgate, all of United Kingdom

[73] Assignee: Smith & Nephew PLC, London, United Kingdom

[21] Appl. No.: 284,415
[22] PCT Filed: Jul. 20, 1994
[86] PCT No.: PCT/GB94/01573
  § 371 Date: Mar. 2, 1995
  § 102(e) Date: Mar. 2, 1995
[87] PCT Pub. No.: WO95/03018
  PCT Pub. Date: Feb. 2, 1995

[30] Foreign Application Priority Data

Jul. 21, 1993 [GB] United Kingdom .......... 9315110
Jul. 21, 1993 [GB] United Kingdom .......... 9315138

[51] Int. Cl.⁶ .......... A61F 13/00
[52] U.S. Cl. .......... 424/443; 424/448; 602/58; 602/41
[58] Field of Search .......... 424/443, 448; 602/58, 41

[56] References Cited

U.S. PATENT DOCUMENTS

| 4,499,896 | 2/1985 | Heinecke | 128/156 |
| 4,657,006 | 4/1987 | Rawlings | 128/156 |
| 5,010,883 | 4/1991 | Rawlings | 128/155 |
| 5,244,457 | 9/1993 | Karami | 602/55 |
| 5,328,450 | 7/1994 | Smith | 602/59 |

*Primary Examiner*—D. Gabrielle Phelan
*Attorney, Agent, or Firm*—Larson and Taylor

[57] ABSTRACT

An adhesive dressing suitable for moist wounds includes a first layer comprising a substrate having a layer of pressure sensitive adhesive on a wound facing surface and a second layer comprising a moisture vapour permeable continuous film. The second layer is attached to the non wound facing surface of the first layer at spaced apart intervals thereby to form a plurality of discrete cellular voids between said first and second layers. The first layer has apertures therein to allow passage of liquids therethrough into the cellular voids and total area of the dressing defined by the cellular voids is from 20% to 80% of the total operable area of the dressing.

12 Claims, 1 Drawing Sheet

SURGICAL DRESSING

The present invention relates to adhesive, moisture vapour permeable surgical dressings for use on human bodies, for example in contact with moist wounds. In particular, this invention relates to a dressing comprising plurality of discrete cells and adapted to transmit water into and through each cell.

It is desirable to allow a wound to heal in its moist state, especially if covered with a layer of wound exudate as this state is believed to be capable of accelerating wound healing. The problems with moist wound healing when the wound is covered with a surgical dressing is that a "blister" of exudate can form under the dressing which is not only unsightly and uncomfortable but may also cause the dressing to leak, thereby defeating the aim of sterility. Such an excess of exudate therefore needs to be removed before a harmful blister forms. Normal methods of aspiration however, may also lead to wound infection. Finally, in order to preserve wound healing in a moist environment, it is desirable not to remove all the exudate as a "dry" wound since a slower healing wound would result.

An attempt to overcome these disadvantages has been proposed in which an adhesive coated moisture vapour permeable, liquid water impervious first layer which contains perforations as a wound contacting layer and an imperforate, moisture vapour permeable, liquid water impermeable film attached to the first layer to form a sealed reservoir into which exudate from a wound may pass. Such dressings suffer from the disadvantage that they are only available in pre-formed sizes. It has also been observed that the performance of such dressings has not been as good as might have been expected in that it has been observed that exudate does not pass through the perforations into the reservoir at a rate which is sufficient to prevent 'blister' formation.

We have found that the use of a large number of physically separate small cells of reservoirs results in a dressing having a better performance than dressings comprising a single reservoir. The dressings of the present invention therefore seek to mitigate the disadvantage of blister formation and wound adherence and to offer the additional advantage of being able to cut the dressing to a desired shape or size.

Accordingly the present invention provides an adhesive dressing suitable for moist wounds including a first layer comprising a substrate having a layer of pressure sensitive adhesive on a wound facing surface and a second layer comprising a moisture vapour permeable continuous film, said second layer being attached to the non wound facing surface of the first layer at spaced apart intervals thereby to form a plurality of discrete cellular voids between said first and second layers, wherein the first layer has apertures therein to allow passage of liquids therethrough into the cellular voids and wherein total area of the dressing defined by the cellular voids is from 20% to 80% of the total operable area of the dressing.

Aptly, the adhesive coated first layer has a low uninterrupted moisture vapour permeability. By low moisture vapour permeability is meant an upright (as hereinafter defined) moisture vapour permeability of less than 300 $gm^{-2}$ 24 $hr^{-1}$ preferably less than 200 $gm^{-2}$ 24 $hr^{-1}$ when measured at 37° C. and 100% to 10% relative humidity difference. By an "uninterrupted moisture vapour permeability" is meant the moisture vapour permeability of the material is the absence of holes therethrough i.e. the moisture vapour permeability of the uninterrupted material.

The moisture vapour permeability (MVP) of the materials employed in the present invention may be determined as follows:

Upright MVP Determination

Discs of the material under test are clamped over Payne Permeability Cups (flanged metal cups) using sealing rings and screw clamps. The exposed surface area of the test sample is 10 $cm^2$. Each cup contains approximately 10 ml. of distilled water.

After weighing the cups are placed in a fan assisted electric oven which is maintained at 37° C. The relative humidity within the oven is maintained at approximately 10% by placing 1 kg. of anhydrous 308 mesh calcium chloride on the floor of the oven.

The cups are removed after 24 hours, allowed to cool for 20 minutes and re-weighed. The MVP of the test material is calculated from the weight loss and expressed in units of grams of water per square metre per 24 hours ($gm^{-2}$ 24 $hr^{-1}$).

Inverted MVP Determination

The method described above is employed except that the Payne Cups are inverted in the oven so that the water within the cups is in contact with the test material and the test is only conducted for four hours (the results being extrapolated to 24 hours).

The dressings according to the invention have the advantage of allowing water to evaporate rapidly from the wound area in the presence of an excess of exudate in the environs of the wound but, as the amount of exudate diminishes, so does the rate of evaporation. The use of a low moisture vapour permeable layer in contact with the wound means that when non-exuding or not rapidly exuding the amount of exudate around the wound is enough to keep it moist without causing blistering of the dressing and will not cause the wound to dry out which may result in adherence of the dressing to the wound.

The second layer aptly comprises a moisture vapour permeable continuous film having a moisture vapour permeability which is greater when in contact with liquid water than when not in contact with liquid water.

The continuous film suitably has the following moisture vapour permeability (MVP) characteristics which are determinable by the Payne Cup Method (as described hereinabove): a moisture vapour permeability when in contact with water (herein referred to as 'inverted' moisture vapour permeability'), that is when the Payne Cup is inverted, of not less than 8000 $gm^{-2}$ 24 $hr^{-1}$ measured at 37° C. and 100% to 10% relative humidity difference, and is preferably greater than 10,000 $gm^{-2}$ 24 $hr^{-1}$. The moisture vapour permeability when not in contact with water (herein referred to as 'upright' moisture vapour permeability) will suitably be not more than 4800 $gm^{-2}$ 24 $hr^{-1}$ measured at 37° C. and 100% to 10% relative humidity difference and is preferably less than 4000 $gm^{-2}$ 24 $hr^{-1}$ and more preferably less than 3600 $gm^{-2}$ 24 $hr^{-1}$.

When the continuous film is attached to the first layer to form the dressing, the moisture vapour permeability of the dressing, as measured for example by means of an evaporimeter placed above the surface of the continuous film, when in contact with water or wound exudate will reflect the high value of the continuous film as liquid will pass through the openings in the first layer into the sealed portions or cellular voids (hereinafter referred as "cells") and will be lost by evaporation through the continuous film. However, when the wound no longer produces exudate and the continuous film is not in contact with water the evaporation of moisture vapour will reflect the permeability of the combination of first layer and continuous film. The use of a low moisture vapour permeable adhesive coated first layer means the wound will not dry out and the advantageous moist conditions required for wound healing are not lost.

Polymer materials which are suitable for use as second layer by possessing the desired enhancement of "inverted" moisture vapour permeability, compared to the "upright" moisture vapour permeability, are those containing chemical groups generally considered to be hydrophilic. Such groups include hydroxyl, ether, ester, carboxyl, amine, amide and carbonyl groups. Thus suitable materials include hydrophilic polyurethane, cellulose derivatives, polyether-polyamides, polyamides, crosslinked polyvinyl alcohols and the like.

It has been found that polyether polyurethanes are particularly suitable for use in the formation of such films. Favoured polyether polyurethanes are essentially free of reactive substituents such as hydroxy or carboxy groups. Such polyurethanes for use in this invention include random polymers containing units derived from diolic compounds and di-isocyanates.

The ether units in such hydrophilic polyurethanes for use in this invention may be notionally derivable from ethylene diol and a propylene or butylene diol; that is they will contain $CH_2CH_2O$— units and

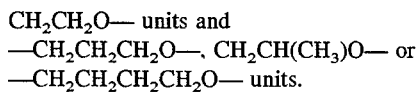  or

—$CH_2CH_2CH_2CH_2O$— units.

Preferably, the ether units in the polyurethane will contain

—$CH_2CH_2O$— and

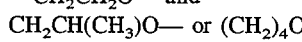 or $(CH_2)_4O$— or mixtures thereof of which poly $CH_2CH(CH_3)O$— blocks are preferred. Desirably, the mole ratio of poly (ethylene glycol) to poly [(prop or but)ylene glycol]-derivable blocks present in the hydrophilic polyurethanes varies between 1:1 to 1:30; preferably from 1:2 to 1:10; and more preferably from 1:2.5 to 1:4. The molecular weights of these blocks is suitably from 600 to 6000 and favourably from 900 to 4000, for example 1000 to 2000.

Preferably, such hydrophilic polyurethanes for use in this invention will contain residues of aliphatic diols of up to 10 carbon atoms and more preferably up to 4 carbon atoms (of which ethane diol is preferred) as chain extenders wherein the mole ratio of diol to polygylcol used in the preparation of the polymer is from 3:1 to 1:4; preferably, 5:2 to 1:3; and more preferably from 2:1 to 1:2.

The hydrophilic polyurethane should contain sufficient di-isocyanate residues to produce the water contents set forth above when the film is hydrated.

The hydrophilic polyurethanes for use in this invention may contain dioisocyanate residues which may be residues of aromatic of aliphatic di-isocyanates such as 4,4'-diphenylmethane di-isocyanate, toluene di-isocyanate, 1,6hexamethylene di-isocyanate or the like. Favoured di-isocyanates for use in the hydrophilic polyurethane of this invention are 4,4'dicyclohexylmethane di-isocyanate (which is preferred) and 4,4-diphenylmethyl di-isocyanate.

As an alternative to the use of aliphatic diol chain extenders, the hydrophilic polyurethane may employ equivalent quantities of aliphatic diamine or aliphatic amino chain extenders of which ethylene diamine is preferred. Similarly somewhat less preferably than using aliphatic diol chain extenders, the hydrophilic polyurethane may employ an aromatic diamine such as phenylenediamine, benzidine or diaminodiphenylmethane.

More preferably, the hydrophilic polyurethane used in a dressing of this invention is essentially a single type of polymer (a product of the polymerisation of the same material) although blends may be employed to form the hydrophilic polyurethane if desired.

Further favoured materials are polyether-polyamide block copolymers whose preparation and properties have for example been described in British Patent No. 1473972, French Patents Nos. 1444437 and 2178205 and U.S. Pat. No. 3,839,243. A particularly apt polyether-polyamide block copolymer is known as Pebax 4011 RN 00 (available from ATO Chemical Products (UK) Ltd.). This polymer has a water content of 55% (approx.) when hydrated and a 'wet-MVP' of >14000 $gm^{-2}$ 24 $hr^{-1}$ and a 'dry-MVP' of 4600 $gm^{-2}$ 24 $hr^{-1}$ for a 70 micron thickness of film at 37° C. and a relative humidity of 100–10%.

Other favoured materials include polyether-polyesters and blends of such polymers. These materials and their production are described in, for example, U.S. Pat. No. 3,763,109. They are commercially available from E J du Pont de Memours also under the trade name HYTREL.

A further suitable, though less preferred material is a plasticised regenerated cellulose film such as cellulose acetate. A suitable film is Raylphane 325P (available from British Sidac Ltd.). This film has an "inverted" MVP of >14000 $gm^{-2}$ 24 $hr^{-1}$ and a 'dry-MVP' of 4100 $gm^{-2}$ 24 $hr^{-1}$ for a 30 micron film when measured at 37° C. and 100–10% relative humidity.

A further suitable, though less preferred material is a polyvinyl alcohol which has been cross-linked, usually be means of heat, to form an insoluble but water absorbent film. A suitable polyvinyl alcohol is available as Polyviol W28/2™ (available from Wacker-Chemie GmbH). This polymer may be cast into a film from aqueous solution, dried and cross-linked using heat for example by autoclaving. This film has a 'wet-MVP' of >13000 $gm^{-2}$ 24 $hr^{-1}$ and a 'dry-MVP' of 4800 (approx.) $gm^{-2}$ 24 $hr^{-1}$ for a 37.5 micron film when measured at 37° C. and 100% to 10% relative humidity difference.

Most suitably the continuous film will be from 15 to 80 μm thick, will more usually be from 20 to 60 μm thick and will preferably be from 22 to 50 μm thick, for example 25, 30 or 40 μm thick.

Suitably also the continuous film will be formed from a hydrophilic polymer which when hydrated contains up to 90% by weight of water, favourably contains 5 to 50% water, more favourably from 10 to 40% of water and preferably from 20 to 30% by weight of water, for example 25% by weight of water.

A preferred hydrophilic polymer is a hydrophilic polyurethane which when hydrated contains from 10 to 40% by weight of water.

Suitable hydrophilic polyurethanes are those which are described in European Patent Application No. 59035 which is incorporated herein by cross reference. A preferred hydrophilic polyurethane is therefore a linear polyether polyurethane which when hydrated contains from 20 to 30% by weight of water.

The dressing of which the continuous film forms part should be flexible and conform readily to the body area to which it is applied. It should also be preferably elastic. Such dressings have the advantage of adhering securely to the body by following the body contours and allowing the body to move without dislodging the dressing. Synthetic polymers are more conformable and elastic than natural polymers which tend to be stiff, inelastic and generally non conformable. Synthetic polymers and especially synthetic elastomeric polymers are therefore preferred for the continuous film.

It is further preferred that the continuous film should be transparent so that the wound may be observed. The continuous film is preferably self supporting, that it is coherent when wet or dry and can be used without recourse to additional support such as fabric, net or the like.

The materials used for the first layer do not themselves have a high moisture vapour permeability. For example the adhesive coated first layer when not possessing holes may have a low moisture vapour permeability, that is a moisture vapour permeability of less than 300 $gm^{-2}$ 24 $hr^{-1}$. Such dressings have been found to provide better conditions for healing of wounds in that moist conditions are maintained as well as low adherency and may be retained in place for extended periods in use which reduces the risk of infection or retraumatisation of the wound whilst it is healing. The low moisture vapour permeability for the adhesive coated first layer may be achieved by either coating a first layer of a relative high moisture vapour permeability with a continuous layer of adhesive of lower moisture vapour permeability or by coating a first layer of low moisture permeability with an adhesive which may be in the form of a continuous, microporous or pattern spread coating which may have a high or low moisture vapour permeability. The relationship between the moist vapour permeabilities of an adhesive coated layer and its component layers being described hereinafter. Thus the skilled man would appreciate which adhesives and which polymer films could be combined to provide a first layer of the correct moisture vapour permeability.

Material suitable for use as the first layer for use in dressings of this invention include elastic or non-elastic, conformable, natural or synthetic polymers. The sheet material of the first layer is adapted to allow transmission of water through the film into the cells, that is it is a water transmitting film by virtue of perforations or holes formed therein. When used herein holes mean any shaped aperture which is usually visible to the naked eye and which passes through the film and the adhesive coat. Such holes communicate only with the cells as no holes extend through the dressing in those regions where the first and second layers are in direct contact with each other.

Materials which are suitable for forming substrate of the first layer and which are permeable to moisture vapour include those which are described in our copending European Patent Application No. 107915 at page 15, lines 5 to 23 and page 16, lines 6 to 16. A favoured first layer is polyurethane. Adhesives suitable for use on skin and for use with such materials to give a low moisture vapour permeability to the adhesive coated material are known in the art and include for example natural or synthetic rubber based adhesives.

Other materials which are suitable for forming the first layer include polyolefin films, such as polyethylene, polybutadiene, polyolefin copolymers, polyisobutylene e.g. Oppanol (Trade Mark of BASF), styrene butadiene styrene block polymers e.g. Kratons (Trade Mark of Shell Chemicals Ltd), polyesters and the like. A first preferred film is a polybutadiene. A more preferred film is made from a styrene-butadiene-styrene triblock copolymer. Another preferred film is made from ethylene-vinyl acetate copolymer.

Suitably the first layer will have a thickness of up to 150 µm, more suitably will be from 15 to 100 µm thick, most suitably will be 20 to 75 µm thick and preferably 25 to 40 µm thick, for example 25 µm, 30 µm, 35 µm or 40 µm.

Suitably a continuous sheet of the material which is adapted to form the first layer will have a moisture vapour permeability of less than 300 $gm^{-2}$ 24 $hr^{-1}$ and more suitably between 20 and 280 $gm^{-2}$ 24 $hr^{-1}$ when measured at 37° C. and 100% to 10% relative humidity. For example some preferred films described hereinafter will have a moisture vapour permeability of between 25 and 90 $gm^{-2}$ 24 $hr^{-1}$ and preferably between 40 and 80 $gm^{-2}$ 24 $hr^{-1}$. A second group of preferred films such as the styrene-butadiene copolymers will have an uninterrupted moisture vapour permeability of 200 to 260 $gm^{-2}$ 24 $hr^{-1}$.

Aptly the number of cells or cellular voids formed in the dressing will be at least 3 per square centimetre, more aptly at least 5 $cm^{-2}$. Suitably the dressing will comprise 20 or more voids $cm^{-2}$. The void area, i.e. the area of the dressing occupied by cells or cellular voids, will comprise at least 20% of the operable area of the dressing and up to 80% of the operable area. Suitably the void area will be at least 30%, more suitably at least 50% of the total operable area.

The first layer will be interrupted by means of apertures or holes, for example circular holes. Alternative configuration for the holes include slits, elipsoidal, triangular, rectangular holes and other polygonal shapes, e.g. hexagonal. Such holes will be capable of allowing the passage of liquid water and normally will be visible to the naked eye and may measure at least 0.1 and may be up to 2.5 mm in at least one dimension, for example 1.5 mm in diameter. Each cell is associated with at least one hole, although cells may be provided with two or more holes, for example four or five holes. Usually the cells and associated holes may be arranged in parallel rows or in staggered rows.

The size of the hole or holes will depend upon the nature of the film comprising the second layer and the presence, absence or nature of any intermediate layers which are hereinafter described and the size and shape of the cell with which it comments.

Aptly the area of the holes or apertures in the first layer (at the wound contacting surface) will comprise 3 to 35% of the total operable surface area of the wound contacting surface of the first layer (by 'operable surface area' is meant that part of the dressing which will be in contact with both skin and the wound and will include areas of the first layer which are sealed to the second layer and areas of the first layer which surround the holes or apertures and define one of the walls of the cells. Aptly the hole area will comprise not more than 25% of the operable surface area, more aptly from 10 to 20% of the total operable area.

The continuous film is attached to the non-wound contacting side of the first layer so as to form a plurality of discrete cells or reservoirs which are capable of holding wound exudate when in use. Each discrete cellular void is surrounded by a peripheral seal area which prevents liquid from directly entering an adjacent cellular void. The attachment means includes heat sealing, ultrasonic welding, radio frequency welding or by means of an adhesive or adhesive tape depending on the nature of the polymers involved. It is preferred that the films are heat sealed together. The sealing may be performed to produce any desired polygonal shaped cell, for example rectangular, triangular or circular. A preferred cell shape is hexagonal.

The area of the second layer which defines the cell wall opposed to the layer which has the hole or holes formed therein is termed 'open' area and is expressed as a percentage of the total operable area of the dressing. (By operable area is meant the total open area of the cells together with the sealed areas between individual cells). The size of the open area is controlled by the width of the sealing areas between cells and the cell geometry and may vary depending upon the proportion required for the dressing. Where a high degree of transparency is required the width of the sealing area may be up to 2 mm. However if a large open area is required, for example for dressings having a second layer of a relatively low vapour permeability the width of the sealing strip may be as little as 0.25 mm. Aptly the width of the sealing area between cells will range from 0.5 to 1.5 mm, more aptly from 0.7 to 1.25 mm.

The selection of open area may also depend on the desired moisture permeability required for the second layer. Where the second layer is bonded to the first layer the moisture vapour permeability will be less than through a single layer of the continuous film. Aptly for films having a moisture vapour transmission rate of about 4000 to 6000 $gm^{-2}$ 24 $hr^{-1}$ when in contact with liquid water the open area can be as much as 80% or more. For films having a higher moisture vapour permeability the open area may be not less than 30%. Suitably the open area will be at least 50%. Generally the open area will also aptly be not more than 75%.

In one embodiment therefore, the continuous film and first layer will be co-extensive and sealed together at least around their edges.

The dressings of the invention will aptly have dimensions of from 5 cm×5 cm to 40 cm×40 cm for example 8 cm×8 cm, 8 cm×12 cm, 10 cm×10 cm, 20 cm×15 cm, 20 cm×30 cm, 40 cm×30 cm and 40 cm×40 cm. It is clear that the size of dressing will be chosen depending upon the size of the wound upon which it is to be used for example the sizes 8 cm×8 cm and 8 cm×12 cm will be used on small wounds while the larger sizes are suitable for donor sites. However it is to be noted that because of their cellular construction, the dressings of the invention may be cut, for example with scissors, to any desired shape or size.

The adhesive employed in the dressings of this invention must be compatible with the wound, that is it must not adhere to it. Suitable adhesives include synthetic polymers or mixtures thereof. Such adhesives may be selected from those described in British Patent Specification No. 1,280,631 and European Patent Application No. 35399. Suitable adhesives are formed from acrylate ester copolymers or polyvinyl ethyl ethers. If desired such adhesives may incorporate an antibacterial agent.

A preferred pressure sensitive adhesive comprises a blend of high and low viscosity polyvinyl ethyl ethers in particular adhesive composition A disclosed in British Patent Specification No. 1280631. Other preferred pressure sensitive adhesives comprise copolymers of acrylate ester with acrylic acid for example as disclosed in European Patent Application No. 35399 and in particular a copolymer of 47 parts by weight of butyl acrylate and 6 parts by weight of acrylic acid with an intrinsic viscosity of at least 1.9 dl/g polymerised in acetone according to the general method given in the above European Application.

Suitably the adhesive is employed at a mass weight per unit of 20 to 80 $gm^{-2}$, more suitably at 20 to 45 $gm^{-2}$ and preferably at 25 to 35 $gm^{-2}$, for example 29 $gm^{-2}$ or 32 $gm^{-2}$.

Suitably the adhesive layer is applied to the film of the first layer as a continuous layer prior to making the holes in the film, so that normally the adhesive layer will be interrupted during interruption of the film.

Alternatively the adhesive layer may be in the form of a pattern spread or discontinuous spread adhesive layer using a conventional surgical adhesive prepared and spread by the method described in for example British Patent No. 819635. The adhesive may also be in the form of a porous or microporous layer.

In a further aspect of the present invention at least some, and preferably all of the cells, contain a water-transmitting material. Suitably an intermediate layer is provided between the non-wound contacting surface of the first layer and the continuous layer. The intermediate layer will be water transmitting so as not to prevent the passage of water from the wound to the continuous film. The presence of the intermediate layer may in certain cases aid the manufacture of the dressing by preventing unwanted adherency of the continuous film to the first layer during, for example, the sterilisation process. The presence of the intermediate layer has further advantages in that it improves the handleability of the dressing and further slows down the rate of the evaporation of the moisture vapour from the surface of the continuous film which reduces the risk that the wound might dry out and stick to the dressing particularly around the holes in the first layer. The intermediate layer also appears to encourage flow of exudate through the holes by means of a wicking action and removes any risk of the first layer and continuous film adhering to each other in use which may prevent operation of the dressing. The intermediate layer may also carry a medicament which is released to the wound area in use. Suitably the medicament will be an antimicrobial agent, for example chlorhexidine or its salts or povidone iodine.

Materials suitable for forming the intermediate layer include woven and non-woven fabrics, nets, perforated films, hydrogels or hydrophilic polymers and the like which are water permeable. Aptly the intermediate layer is a non-woven fabric or a perforated film or an integral net. Preferably the layer is a non-woven fabric. Generally suitable non-woven fabrics will be formed from hydrophobic polymers such a polyolefins. Preferred non-woven fabrics include a spun bonded polypropylene fabric known as Novelin (Trade Mark, available from J. W. Suominen). In the manufacture of the dressings a piece of the non-woven fabric may be placed over the perforated area of the first layer, the continuous film placed on top of the non-woven fabric and all three layers sealed together around their edges or the continuous film may be simply only sealed to the first layer, thereby trapping the intermediate layer between the two.

Films, which when perforated, are suitable for use as an intermediate layer include polyolefin films and polyester films such as Melinex (Trade Mark, available from ICI plc.) Aptly these intermediate layers are perforated in a similar manner to the first layer as described hereinbefore, that is they are perforated with holes or slits. It has been found that it is advantageous in maintaining the moistness of the wound and to the progress of wound healing if the perforations in the intermediate layer are not in register with the apertures in the first layer.

Aptly when an intermediate layer is present, this layer is also transparent so that the progress of wound healing may be observed. However, in the case where the layer is a non-woven fabric the fabric may be removed prior to sealing between the continuous film and the first layer so that the wound may still be observed.

When the intermediate layer of water transmitting material is in the form of a polymeric film then it may have a thickness similar to that used for the interrupted film that is up to 150 microns. If the intermediate layer is a non-woven fabric then the layer tends to be thicker.

Thus in a further aspect the present invention provides an adhesive dressing suitable for use on moist wounds which dressing comprises a pressure sensitive adhesive-coated first layer which has holes therethrough capable of transmitting liquid water and a moisture vapour permeable continuous film attached to the first layer thereby forming a reservoir into which water can pass and evaporate therefrom which dressing is characterised in that the adhesive coated first layer has a moisture vapour permeability of less than 300 gm$^{-2}$ 24 hr$^{-1}$ and the moisture vapour permeable continuous film has a moisture vapour permeability which is greater when in contact with liquid water than when not in contact with liquid water and that there is a further water transmitting intermediate layer present between the first layer and the continuous film.

The materials which may comprise the continuous film and first layer are as hereinbefore described.

Optionally the first layer may also incorporate or may have attached to its surface remote from the continuous film a water-absorbing material such as a hydrogel such as Spenco (Trade Mark) or a hydrophilic foam such as Hypol (Trade Mark) foam. The presence of such a material does not interfere with the escape of excess water but provides a reservoir of exudate which remains.

As the amount of wound exudate increases, tending to blister-formation, the exudate seeps through the holes, hydrating the continuous film layer, the MVP of which increases so the water evaporates. Once the "blister" has subsided, the MVP of the continuous film decreases, but the wound still remains moist because most of its area is covered by the less permeable first layer.

Therefore in a further aspect the present invention provides a method of dressing an exuding wound on an animal body comprising placing over the wound a dressing of the present invention and adhering the dressing to the body and allowing the wound exudate to pass through the holes of the first layer into a reservoir and allowing a moisture vapour from said exudate to escape by transmission through the continuous film.

In a preferred aspect the present invention provides a method of dressing a donor site on an animal body which comprises placing over the donor site a dressing of the present invention and adhering the dressing to the body and leaving in position for a period of from 3 to 20 days.

Dressings of the present invention are suitable for use on wounds including donor sites (split thickness), partial thickness burns and leg ulcers, which wounds exude large quantities of liquid and heal by re-epithelialisation. Many of these wounds will normally be dressed for a period of from 3 to 20 days and preferably for 7 to 14 days, when re-epithelialisation of the wound should be complete. However leg ulcer healing may take months before re-epithelialisation is complete and it is likely that such ulcers will be dressed continually during that time.

Thus in particularly preferred aspect the present invention provides a method of dressing a donor site on an animal body which comprises placing over the donor site a dressing of the present invention and adhering the dressing to the body and leaving in position for a period of from 7 to 14 days.

In a preferred method the dressing will have an intermediate layer between the adhesive coated first layer and the continuous film.

The dressings used in the method of dressing an exuding wound may be any of those hereinbefore described.

The method of dressing a wound using a dressing of the present invention may be applied to all exuding wounds such as burns, skin graft donor sites, pressure sores, ulcers, surgical wounds and the like. It is an advantage of the dressing of the present invention that they may be left in place on the wound for extended periods of time with reduced risk of leaking, causing blister formation or adhering to the wound. The time over which a dressing may be left in place will vary depending on the type of wound and the form of any other treatment which may be given to the wound. A dressing may be left covering a skin graft donor site for up to 14 days without detrimental effect and can yield a healed wound at the end of that time.

Preferably, the dressing according to this invention is provided in sterilised form and, when self-adhesive, is adhered to a removable sterile backing sheet. Suitable removable backing sheets or release liners are those which are conventionally used in the art, that is release liners which are made of, or coated with polyethylene, polypropylene and fluorocarbons and silicone-coated release papers or polyester films. A preferred release line is formed from silicone-coated paper. Prior to use, the release liner is stripped from the adhesive coating of the dressing so that the dressing may then be applied to the skin. The dressing may be packaged in a bacteria-proof package such as a paper, plastic or aluminium foil pouch and sterilisation may be achieved in conventional manner, e.g. by use of gamma irradiation, heat or ethylene oxide.

Suitable forms of dressing and removable backing sheet (s) include ones similar to those described in European Patent Specification No. 51-935. Suitable hydrophilic polyurethanes for use include those described in European Patent Specification No. 50035.

One form of a dressing of the present invention the adhesive coated first layer may extend beyond the edges of the continuous film on two opposite sides. The extended margins of the first layer may then be adhered to a non-adhesive polymer film, such as a polyester film, to form non-adhesive handles to aid the manipulation of the dressing when positioning on the body.

The polymer which is to form the non-adhesive layer or backing layer of the first layer may be extruded or cast (from a solution) onto a silicone release paper to give a film of the required thickness and weight when the solvent is removed. An adhesive film may be similarly cast on to a release paper. The backing layer may be transferred to the adhesive film by conventional transfer coating means. Alternatively the first layer may be cast onto one surface of a double sided release paper and the adhesive layer cast onto the first layer. The combined layers are then transferred to the other surface of the release paper so that the adhesive layer is covered by the release paper. The handles may be inserted during this transfer process. The combined films may then be formed into the first layer by punching holes of the appropriate diameter through the backing and adhesive layers and release paper. Alternatively slits of the appropriate length and shape may be cut through the backing layer and adhesive layer and release paper using a sharp blade or an array of such blades which give the correct pattern.

The continuous film may be cast from a solution of the appropriate hydrophilic polymer at the required thickness and weight. This film may be heat sealed or adhered around its edges to the non-adhesive side of the first layer. In other instances the continuous film may be formed by extrusion of the appropriate polymer to give a film of the required thickness. The continuous film may be sealed using a heated box-section so that the holes of the first layer fall within the sealed square so formed. Other dressings according to this invention may be prepared by methods known as those skilled in the art.

The dressings may be formed to any appropriate size using the general preparative method described above. Dressings of smaller size may be cut from larger dressings.

BRIEF DESCRIPTION OF THE DRAWINGS

The invention will be further described with reference to the accompanying drawings in which.

Figure 1:
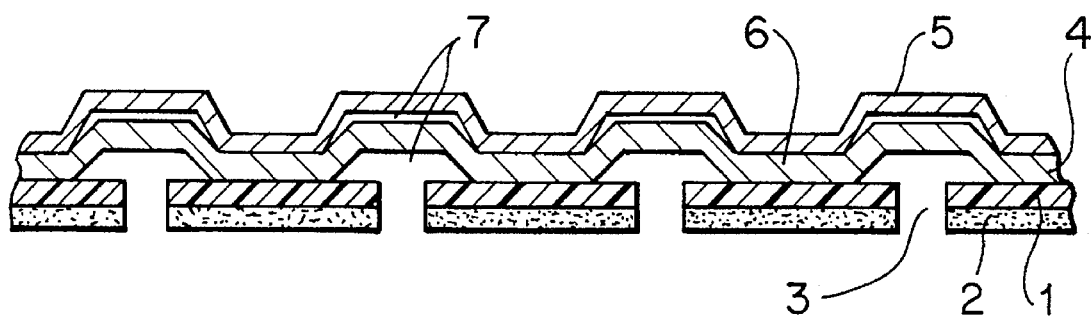
FIG. 1 is schematic sectional view of a dressing in accordance with the invention taken through line A—A of FIG. 2 which schematically represents a plan view of such a dressing.
Figure 2:
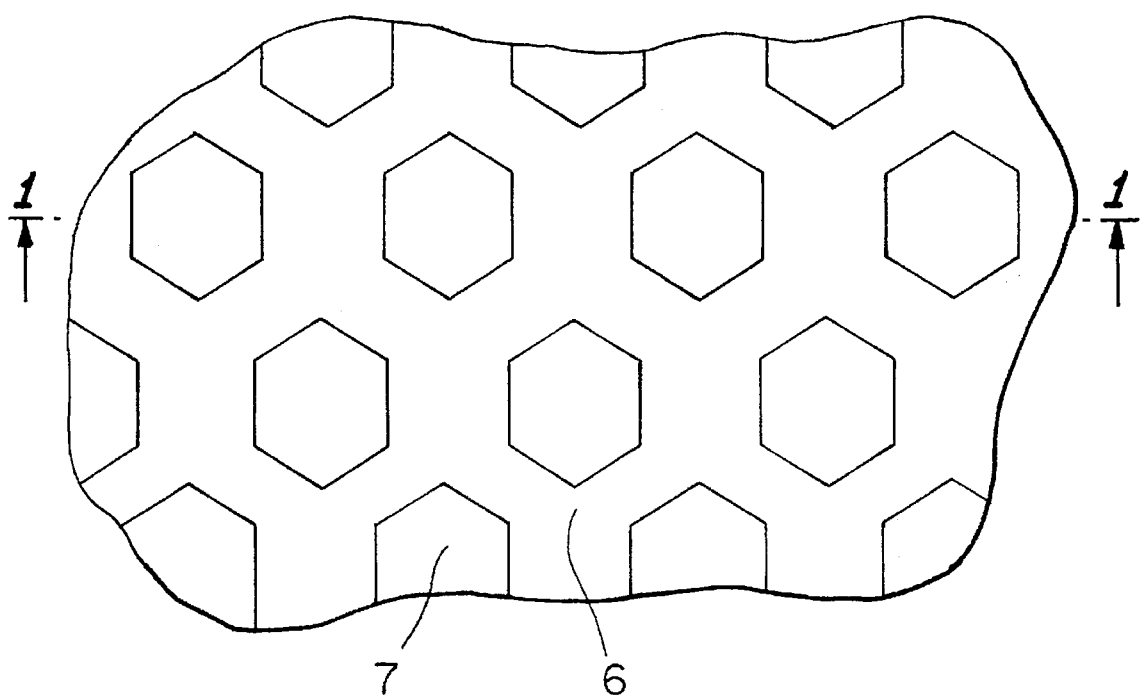

The dressing comprises a wound facing layer 1 coated on its wound facing side with an adhesive layer 2. Layers 1 and 2 which form the first layers are provided with holes 3.

A continuous film 5 comprising the second layer and an absorbent intermediate layer 4 are bonded at areas 6 to the non-wound facing surface of layer 1. The bonding arrangement 6 forms non-bonded hexagonally shaped areas of cells 7 each having at least one hole associated therewith.

The invention is further illustrated by the following example.

EXAMPLE

A dressing in accordance with the invention (Sample X) was constructed having the following properties.

| Dressing Size (Operable Area) | | $10 \times 10$ cm |
|---|---|---|
| No of Cells | | about 440 |
| First Layer | Substrate | EVA/HIPS ① |
| | Thickness | 25μ (nominal) |
| | Adhesive | Vinyl Ether ② |
| | Weight | 30–60 gm$^{-2}$ |
| Upright MVP | | 200 gm$^{-2}$ 24 hr$^{-1}$ |
| Second Layer | Material | Hydrophilic Polyurethane ③ |
| | Thickness/ Weight | 30 gm$^{-2}$ |
| Upright MVP | | 1500 gm$^{-2}$ 24 hr$^{-1}$ |
| Inverted MVP | | 1200 gm$^{-2}$ 24 hr$^{-1}$ |
| Intermediate Layer Laminate | Material Weight | Demique ④ 1 oz yd$^{-2}$ (40 gm$^{-2}$) |
| Cell Shape | | Regular Hexagonal |
| Cell Size (across face) | | 3.75 mm |
| Seal Width | | 1.00 mm |
| Perforation Shape | | Round |
| Perforation Dimension (Mean Diameter) | | 0.65 mm |
| Total Aperture Area | | 16.5% ⑤ |

Note ① - a polymer blend (20/80) ethylene-vinyl acetate copolymer (sold under the Trade name EVATANE 10 20 VN5) and high impact polystyrene (sold under the trade name STYRON 485).
Note ② - a polyvinyl ether adhesive described in European Patent No. 0194881
Note ③ - a hydrophilic polyurethane produced as described in Example 1 of UK Patent No. 2093190
Note ④ - a non-woven fabric sold by Kimberley-Clark
Note ⑤ - measured as a percentage of the total operable area.

An 80 year old white female had a venous ulcer (measuring about 3×2 cm) on the inside of the left leg in the ankle region.

A commercially available 10×10 cm moisture vapour permeable continuous film dressing conventionally employed for covering ulcers was applied over the ulcer and left for 24 hrs. The condition of the ulcer was examined at regular intervals over the 24 hr period. Within the first half an hour there was evidence of build up of exudate under the dressing. After several hours exudate was beginning to track towards the edge of the dressing and there was evidence of maceration of the healthy skin around the ulcer under the dressing. After 24 hours exudate was leaking from the dressing and an area of skin under the dressing, which surrounded the ulcer and was equivalent to the area the ulcer, was severely macerated.

The dressing was then changed and Sample X applied to the same area as the original film dressing. Examination of the dressing, after a few hours showed that the cells immediately over the ulcer were visibly distended, demonstrating the exudate was readily passing into the cells.

Twenty four hours after the Sample X dressing was applied the dressing was examined for a final time. It was observed that no leakage had occurred and that exudate had entered the two rows of cells around the outside of the periphery of the ulcer. Upon removal of the dressing not only was no maceration of healthy skin observed but also the previously macerated areas had returned to a healthy condition. During the forty eight hour test the overall size of the ulcer had not increased.

We claim:

1. An adhesive dressing comprising a first comprising a substrate having a layer of adhesive on a wound facing surface and a second layer comprising a moisture vapour permeable continuous film, said second layer being attached to the non-wound facing surface of the first layer at spaced apart intervals thereby to form a plurality of discrete cellular voids between said first and second layers, wherein each cellular void is surrounded by a peripheral seal area, which seal area prevents liquid from directly entering an adjacent cellular void, wherein the first layer has apertures therein to allow the passage of liquids therethrough into the cellular voids and wherein the total area defined by the cellular voids is from 20 to 80% of the total operable area of the dressing.

2. A dressing according to claim 1 wherein the uninterrupted moisture vapour of the first layer is less than 300 gm$^{-2}$ 24 hr$^{-1}$ when measured at 37° C. at 100% to 10% relative humidity difference.

3. A dressing according to claim 1 wherein number of cellular voids is not less than 4 cm$^{-2}$.

4. A dressing according to claim 1 wherein the upright moisture vapour permeability of the second layer is greater when in contact with liquid water than when in contact with water vapour.

5. A dressing as claimed in claim 4 wherein the inverted moisture vapour permeability of the second layer is not less than 8000 gm$^{-2}$ 24 hr$^{-1}$ and the upright moisture vapour permeability is not more than 4800 gm$^{-2}$ 24 hr$^{-1}$.

6. A dressing according to claim 1 wherein each aperture is at 0.1 mm wide in at least one dimension.

7. A dressing according to claim 1 wherein total area defined by the apertures in the first layer is from 3 to 35% of the total operable area of the first layer.

8. A dressing according to claim 1 wherein the open area of the second layer is not more than 75% of the total operable area of the second layer.

9. A dressing as claimed in claim 1 wherein at least some of the cellular voids contain a water-transmitting material.

10. A dressing according to claim 9 wherein an intermediate layer of a water-transmitting material is arranged between said first and second layer of the dressing.

11. A dressing according to claim 10 wherein the intermediate layer comprises a non-woven fabric.

12. A dressing according to claim 1 wherein the adhesive layer comprises a pattern spread net or grid of lines of adhesive, wherein said lines register with the non-apertured portions of the first layer substrate.

* * * * *